US006713259B2

(12) United States Patent
Levine

(10) Patent No.: US 6,713,259 B2
(45) Date of Patent: Mar. 30, 2004

(54) CORN EVENT MON810 AND COMPOSITIONS AND METHODS FOR DETECTION THEREOF

(75) Inventor: Elaine B. Levine, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/951,470

(22) Filed: Sep. 13, 2001

(65) Prior Publication Data

US 2002/0102582 A1 Aug. 1, 2002

Related U.S. Application Data

(60) Provisional application No. 60/232,208, filed on Sep. 13, 2000.

(51) Int. Cl.[7] .......................... C12Q 1/68; C12P 19/34; C07H 21/02; C07H 21/04
(52) U.S. Cl. ........................ 435/6; 435/9.2; 536/23.1; 536/24.3
(58) Field of Search ..................... 435/6, 91.2, 455; 536/24.3, 23.6, 24.33; 514/12; 800/278, 288

(56) References Cited

U.S. PATENT DOCUMENTS

| 5,500,365 A | 3/1996 | Fischhoff et al. |
| 5,554,592 A | * 9/1996 | Quistad et al. ............... 514/12 |
| 5,880,275 A | 3/1999 | Fischhoff et al. |

FOREIGN PATENT DOCUMENTS

| GB | WO 98/04737 | * 2/1998 | ............ C12Q/1/68 |
| WO | WO 90/10076 | 9/1990 | |
| WO | WO 97/32028 | * 9/1997 | ............ C12N/15/82 |

OTHER PUBLICATIONS

Ahern, A, Jul. 1995, The Scientist Inc., vol. 9, 1–5.*
Zimmermann et al., Jul. 1998, LWT, 31, 664–667.*

* cited by examiner

*Primary Examiner*—Carla J. Myers
*Assistant Examiner*—Sally Sakelaris
(74) *Attorney, Agent, or Firm*—Timothy K. Ball; Dennis R. Hoerner

(57) ABSTRACT

The present invention provides corn that includes the MON810 event, which confers resistance to Lepidopteran insect damage. Also provided are assays for detecting the presence of the MON810 event based on the DNA sequence of the recombinant construct inserted into the corn genome that resulted in the MON81O event and of genomic sequences flanking the insertion site.

13 Claims, No Drawings

SEQUENCE LISTING

```
<160> NUMBER OF SEQ ID NOS: 10

<210> SEQ ID NO 1
<211> LENGTH: 20
<212> TYPE: DNA
<213> ORGANISM: corn
<220> FEATURE:
<221> NAME/KEY: DNA
<222> LOCATION: (1)..(20)
<223> OTHER INFORMATION: 5' genome-insert junction

<400> SEQUENCE: 1
acatcctttg ccattgccca                                              20

<210> SEQ ID NO 2
<211> LENGTH: 20
<212> TYPE: DNA
<213> ORGANISM: corn
<220> FEATURE:
<221> NAME/KEY: DNA
<222> LOCATION: (1)..(20)
<223> OTHER INFORMATION: 3' insert-genome junction

<400> SEQUENCE: 2
gaacgaggac tttcggtagc                                              20

<210> SEQ ID NO 3
<211> LENGTH: 566
<212> TYPE: DNA
<213> ORGANISM: corn
<220> FEATURE:
<221> NAME/KEY: DNA
<222> LOCATION: (1)..(566)
<223> OTHER INFORMATION: 5' genome+insert sequence

<400> SEQUENCE: 3
tcaagccgaa ggtacatctg taatttgata tcatttctat tcttccatga taataaaata    60
```

```
gaaataagtt gattataata tataattgtt tatgttatct cttatacttc atatgattcc     120
ttcttcatta ttatatcttg tgctgatgaa ggtatgtcct tcataacctt cgcccgaaaa     180
tcattatatc ccaagggaaa taatgcttcg aaggacgaag gactctaacg tttaacatcc     240
tttgccattg cccagctatc tgtcacttta ttgtgaagat agtggaaaag gaaggtggct     300
cctacaaatg ccatcattgc gataaaggaa aggccatcgt tgaagatgcc tctgccgaca     360
gtggtcccaa agatggaccc ccacccacga ggagcatcgt ggaaaagaa gacgttccaa      420 ccacgtcttc aaagcaagtg gattgatgtg atatctccac tgacgtaagg gatgacgcac     480
aatcccacta tccttcgcaa gacccttcct ctatataagg aagttcattt catttggaga     540
ggacacgctg acaagctgac tctagc                                          566
```

```
<210> SEQ ID NO 4
<211> LENGTH: 879
<212> TYPE: DNA
<213> ORGANISM: corn
<220> FEATURE:
<221> NAME/KEY: DNA
<222> LOCATION: (1)..(879)
<223> OTHER INFORMATION: 3' insert+genome sequence

<400> SEQUENCE: 4
```

```
ttcgacgag tgctacccta cctacttgta ccatgaagaa tcgatgagtc agctaaggct       60
tacactcgct accagctccg cggctacatc gaagacagcc aagacctcga gatttacctg     120
atccgctaca acgccaagca cgagaccgtc aacgtgcccg gtactggttc cctctggccg     180
ctgagcgccc ccagcccgat cggcaagtgt gcccaccaca gccaccactt ctccttggac     240
atcgatgtgg gctgcaccga cctgaacgag gactttcggt agccttcttt catttccgaa     300
tttgcttgcg agcagtcagg tccttttgat tcatctgagt ttggctttac aatagctttt     360
ccttttcctt tggcagtact agtgctttca tcatgagaat ccttcttaga tgtaagacca     420
cctgcagcag atgactttga tcttgttgtt gggcgccgac cagattgagc cattgcagct     480
gttaatgatg caccagccgt ggtgccagga accccagatt cagaattatt accagatgga     540
attataggct tcgatgcaac ctcactgcgt tgaactctag gccaaaggaa ttcttcaaca     600
gatgcaagac tagcaaatgg gtcgataagc acaatatttg atgaataatc ccgaagtgat     660
ttttcgcctt gagctcggga agacgaagc ttgaagggtt gagccagagc actaagacct      720
gaagtcagac gagaccctcc aataccaatc ctactagact ggctgagcac aacagggaaa     780
cgttccagcg aagacaatgc actttgcagt ttctaaccaa cagtgccatg gagtttcatt     840
ctcgtccatg atcaatagaa agggcaacag atatgaagg                            879
```

```
<210> SEQ ID NO 5
<211> LENGTH: 244
<212> TYPE: DNA
<213> ORGANISM: corn
<220> FEATURE:
<221> NAME/KEY: DNA
<222> LOCATION: (1)..(244)
<223> OTHER INFORMATION: 5' flanking corn genome

<400> SEQUENCE: 5
```

```
tcaagccgaa ggtacatctg taatttgata tcatttctat tcttccatga taataaaata     60
gaaataagtt gattataata tataattgtt tatgttatct cttatacttc atatgattcc     120
ttcttcatta ttatatcttg tgctgatgaa ggtatgtcct tcataacctt cgcccgaaaa     180
```

```
tcattatatc ccaagggaaa taatgcttcg aaggacgaag gactctaacg tttaacatcc    240
tttg                                                                244

<210> SEQ ID NO 6
<211> LENGTH: 606
<212> TYPE: DNA
<213> ORGANISM: corn
<220> FEATURE:
<221> NAME/KEY: DNA
<222> LOCATION: (1)..(606)
<223> OTHER INFORMATION: 3' flanking corn genome

<400> SEQUENCE: 6
tttcggtagc cttctttcat ttccgaattt gcttgcgagc agtcaggtcc ttttgattca     60
tctgagtttg gctttacaat agcttttcct tttcctttgg cagtactagt gctttcatca    120
tgagaatcct tcttagatgt aagaccacct gcagcagatg actttgatct tgttgttggg    180
cgccgaccag attgagccat tgcagctgtt aatgatgcac cagccgtggt gccaggaacc    240
ccagattcag aattattacc agatggaatt ataggcttcg atgcaacctc actgcgttga    300
actctaggcc aaaggaattc ttcaacagat gcaagactag caaatgggtc gataagcaca    360
atatttgatg aataatcccg aagtgatttt tcgccttgag ctcgggaaag acgaagcttg    420
aagggttgag ccagagcact aagacctgaa gtcagacgag accctccaat accaatccta    480
ctagactggc tgagcacaac agggaaacgt tccagcgaag acaatgcact ttgcagtttc    540
taaccaacag tgccatggag tttcattctc gtccatgatc aatagaaagg gcaacagata    600
tgaagg                                                              606

<210> SEQ ID NO 7
<211> LENGTH: 18
<212> TYPE: DNA
<213> ORGANISM: Artificial Sequence
<220> FEATURE:
<221> NAME/KEY: DNA
<222> LOCATION: (1)..(18)
<223> OTHER INFORMATION: 5' flanking 5' PCR primer

<400> SEQUENCE: 7
tcaagccgaa ggtacatc                                                  18

<210> SEQ ID NO 8
<211> LENGTH: 21
<212> TYPE: DNA
<213> ORGANISM: Artificial Sequence
<220> FEATURE:
<221> NAME/KEY: DNA
<222> LOCATION: (1)..(21)
<223> OTHER INFORMATION: 5' flanking 3' PCR primer

<400> SEQUENCE: 8
cgctgacaag ctgactctag c                                              21

<210> SEQ ID NO 9
<211> LENGTH: 28
<212> TYPE: DNA
<213> ORGANISM: Artificial Sequence
<220> FEATURE:
<221> NAME/KEY: DNA
<222> LOCATION: (1)..(28)
<223> OTHER INFORMATION: 3' flanking 5' PCR primer

<400> SEQUENCE: 9
tttcgacgag tgctacccta cctacttg                                       28
```

-continued

```
<210> SEQ ID NO 10
<211> LENGTH: 28
<212> TYPE: DNA
<213> ORGANISM: Artificial Sequence
<220> FEATURE:
<221> NAME/KEY: DNA
<222> LOCATION: (1)..(28)
<223> OTHER INFORMATION: 3' flanking 3' PCR primer

<400> SEQUENCE: 10
tcaatagaaa gggcaacaga tatgaagg                                            28
```

US 6,713,259 B2

CORN EVENT MON810 AND COMPOSITIONS AND METHODS FOR DETECTION THEREOF

CROSS REFERENCE TO RELATED APPLICATIONS

This application claims the benefit of priority to U.S. Provisional Application Ser. No. 60/232,208 filed Sep. 13, 2000.

FIELD OF THE INVENTION

This invention relates to the field of plant molecular biology, more specifically to the invention of a DNA construct for conferring improved insect resistance to a corn plant, and even more specifically to an insect resistant corn plant transformation event MON810 and progeny thereof, and to assays for detecting the presence of MON810 DNA in a sample and compositions thereof.

BACKGROUND OF THE INVENTION

As used herein, the term "event" refers to a plant produced by transformation and regeneration of a single plant cell with heterologous DNA, i.e., a DNA construct that includes a transgene of interest. Normally, transformation of plant tissue produces multiple events, each of which represent insertion of a DNA construct into a different location in the genome each of a plant cell. Based on the expression of the transgene or other desirable characteristics, a particular event is selected.

The expression of foreign genes in plants is known to be influenced by their chromosomal position, perhaps due to chromatin structure (e.g., heterochromatin) or the proximity of transcriptional regulation elements (e.g., enhancers) close to the integration site (Weising et al., 1988, "Foreign Genes in Plants," Ann. Rev. Genet. 22:421–477). For this reason, it is often necessary to screen a large number of events in order to identify an event characterized by optimal expression of an introduced gene of interest. For example, it has been observed in plants and in other organisms that there may be wide variations in levels of expression of a heterologous gene introduced into the chromosome of a plants' genome among individually selected events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for example. It is possible to detect the presence of a transgene by any well known nucleic acid detection method including but not limited to thermal amplification (PCR™) or DNA hybridization using nucleic acid probes. Typically, for the sake of simplicity and uniformity of reagents and methodologies for use in detecting a particular DNA construct that has been used for transforming various plant varieties, these detection methods generally focus on frequently used genetic elements, such as promoters, terminators, marker genes, etc., because for many DNA constructs, the coding sequence region is interchangeable. As a result, such methods may not be useful for discriminating between constructs that differ only with reference to the coding sequence. In addition, such methods may not be useful for discriminating between different events, particularly those produced using the same DNA construct unless the sequence of chromosomal DNA adjacent to the inserted heterologous DNA ("flanking DNA") is known. An event-specific thermal amplification (PCR™) assay is discussed, for example, by Windels et al. (Med. Fac. Landbouww, Univ. Gent 64/5b:459–462, 1999), who identified glyphosate tolerant soybean event 40-3-2 using a thermal amplification primer set spanning the junction between the insert and flanking DNA. Specifically, one primer was comprised of sequence from within the insert and a second primer was comprised of sequence from flanking DNA.

The inventor herein discloses novel and useful isolated nucleic acid sequences, as well as methods for detecting these nucleic acids in a biological sample, and kits comprising the reagents necessary for use in detecting these nucleic acids in a biological sample.

SUMMARY OF THE INVENTION

The inventor herein has discovered a corn event, MON810, that is resistant to Lepidopteran insect infestation, and also provides compositions and methods for detecting the presence of genomic DNA from this event in a biological sample.

According to one aspect of the invention, DNA sequences are provided that comprise at least one junction sequence of corn event MON810 selected from the group consisting of 5'-ACATCCTTTGCCATTGCCCA-3' (SEQ ID NO:1) and 5'-GAACGAGGACTTTCGGTAGC-3' (SEQ ID NO:2) and complements thereof (i.e., one or both junction sequences), wherein a junction sequence spans the junction between heterologous DNA inserted into the corn genome and DNA from the corn genome flanking the insertion site and is diagnostic for the event. Included are DNA sequences that comprise at least 10 or more (e.g., 15, 25, 50) nucleotides of insert sequence from corn event MON810 and similar length of flanking DNA from corn event MON810. Also included are DNA sequences which comprise 15 or more nucleotides of contiguous insert sequence from corn event MON810 and at least one nucleotide of flanking DNA from corn event MON810 adjacent to the insert sequence. Such DNA sequences are diagnostic for corn event MON810. Nucleic acid amplification of genomic DNA from the event produces an amplicon comprising such diagnostic DNA sequences.

According to another aspect of the invention, corn plants comprising such DNA sequences and seed from such corn plants are provided.

According to another aspect of the invention, flanking sequence primers for detecting corn event MON810 are provided. Such flanking sequence primers comprise an isolated nucleic acid sequence comprising at least 15 contiguous nucleotides from nucleotides 1–244 of SEQ ID NO:3 (arbitrarily designated herein as the 5' flanking sequence), at least 15 contiguous nucleotides from nucleotides 274–879 of SEQ ID NO:4 (arbitrarily designated herein as the 3' flanking sequence), or the complements thereof.

According to another aspect of the invention, primer sets that are useful for nucleic acid amplification, for example, are provided. Such primer sets comprise a primer comprising a nucleotide sequence of at least 10–15 contiguous nucleotides in length which is or is complementary to one of the above-described genomic flanking sequences (SEQ ID NO:3 or SEQ ID NO:4) and a second primer comprising at least an isolated 10–15 contiguous nucleotides of heterologous DNA inserted into the plant DNA sequence, i.e., the DNA sequence inserted into the recombinant corn plant event MON810. The second primer is preferably a polynucleotide sequence which is or is complementary to the insert sequence adjacent to the plant genomic flanking DNA sequence as set forth in SEQ ID NO:3 from nucleotide position 245 through 566 and in SEQ ID NO:4 from nucleotide position 1 through 273. Of course, it is well within the skill in the art to obtain additional sequence further out into the genome sequence flanking either end of the inserted heterologous DNA sequence for use as a primer sequence that can be used in such primer pairs for amplifying the sequences that are diagnostic for the MON810 corn event. For the purposes of this disclosure, the phrase "further out into the genome sequence flanking either end of the inserted heterologous DNA sequence" refers specifically to a sequential movement away from the ends of the inserted heterologous DNA sequence, the points at which the inserted DNA sequence is adjacent to native genomic DNA sequence, and out into the genomic DNA of the particular chromosome into which the heterologous DNA sequence was inserted. Preferably, a primer sequence corresponding to or complementary to a part of the insert sequence should prime the transcriptional extension of a nascent strand of DNA or RNA toward the nearest flanking sequence junction. Consequently, a primer sequence corresponding to or complementary to a part of the genomic flanking sequence should prime the transcriptional extension of a nascent strand of DNA or RNA toward the nearest flanking sequence junction. A primer sequence can be, or can be complementary to, a heterologous DNA sequence inserted into the chromosome of the plant, or a genomic flanking sequence. One skilled in the art would readily recognize the benefit of whether a primer sequence would need to be, or would need to be complementary to, the sequence as set forth within the inserted heterologous DNA sequence or as set forth in SEQ ID NO:3 or SEQ ID NO:4 depending upon the nature of the product desired to be obtained through the use of the nested set of primers intended for use in amplifying a particular flanking sequence containing the junction between the genomic DNA sequence and the inserted heterologous DNA sequence.

According to another aspect of the invention, methods of detecting the presence of DNA corresponding to the corn event MON810 in a biological sample are provided. Such methods comprise: (a) contacting the sample comprising DNA with a primer set that, when used in a nucleic-acid amplification reaction with genomic DNA from corn event MON810, produces an amplicon that is diagnostic for corn event MON810; (b) performing a nucleic acid amplification reaction, thereby producing the amplicon; and (c) detecting the amplicon.

According to another aspect of the invention, one method of detecting the presence of a DNA corresponding to the MON810 event in a biological sample comprises: (a) contacting the biological sample comprising DNA or RNA with a probe that hybridizes under stringent hybridization conditions with genomic DNA from corn event MON810 and does not hybridize under the same stringent hybridization conditions with DNA from a control corn plant; (b) subjecting the sample and probe to stringent hybridization and wash conditions; and (c) detecting hybridization of the probe to the DNA. Detection can be by any means well known in the art including but not limited to fluorescent, chemiluminescent, radiological, immunological, or otherwise. In the case in which hybridization is intended to be used as a means for amplification of a particular sequence to produce an amplicon which is diagnostic for the MON810 maize event, the production and detection by any means well known in the art of the amplicon is intended to be indicative of the intended hybridization to the target sequence where one probe or primer is utilized, or sequences where two or more probes or primers are utilized. The term "biological sample" is intended to comprise a sample that contains or is suspected of containing a nucleic acid comprising from between five and ten nucleotides either side of the point at which one or the other of the two terminal ends of the inserted heterologous DNA sequence contacts the genomic DNA sequence within the chromosome into which the heterologous DNA sequence was inserted, herein also known as the junction sequences. In addition, the junction sequence comprises as little as two nucleotides: those being the first nucleotide within the flanking genomic DNA adjacent to and covalently linked to the first nucleotide within the inserted heterologous DNA sequence.

Another aspect of the present invention is methods and compositions for detecting the presence of a target site, i.e., at least one of the junctions of the insert DNA with the genomic DNA of the corn plant in MON810, in a sample of nucleic acid derived from or obtained from the genome of the MON810 event, using a variety of detection methods including TAQMAN (Perkin Elmer), thermal amplification, ligase chain reaction, southern hybridization, ELISA methods, and colorimetric and fluorescent detection methods. In particular the present invention provides for kits for detecting the presence of the target sequence, i.e., at least one of the junctions of the insert DNA with the genomic DNA of the corn plant in MON810, in a sample containing genomic nucleic acid from MON810. The kit is comprised of at least one polynucleotide capable of binding to the target site or substantially adjacent to the target site and at least one means for detecting the binding of the polynucleotide to the target site. The detecting means can be either fluorescent, chemiluminescent, colorimetric, or isotopic and can be coupled at least with immunological methods for detecting the binding. A kit is also envisioned which can detect the presence of the target site in a sample, i.e., at least one of the junctions of the insert DNA with the genomic DNA of the corn plant in MON810, taking advantage of two or more polynucleotide sequences which together are capable of binding to nucleotide sequences adjacent to or within about 100 base pairs, or within about 200 base pairs, or within about 500 base pairs or within about 1000 base pairs of the target sequence and which can be extended toward each other to form an amplicon which contains at least the target site.

According to another aspect of the invention, methods of detecting the presence of DNA corresponding to the maize event MON810 in a sample are provided. Such methods comprise: (a) contacting the sample comprising DNA with a primer set that, when used in a nucleic-acid amplification reaction with genomic DNA from maize event MON810, produces an amplicon that is diagnostic for maize event MON810; (b) performing a nucleic acid amplification reaction, thereby producing the amplicon; and (c) detecting the amplicon.

According to another aspect of the invention, a kit is provided for the detection of maize event MON810. The kit includes at least one DNA sequence of sufficient length of polynucleotides which is or is complementary to SEQ ID NO:1 or SEQ ID NO:2, wherein the DNA sequences are useful as primers or probes that hybridize to isolated DNA from maize event MON810 or its progeny, and which, upon hybridization to a nucleic acid sequence in a sample followed by detection of the hybridization to the target sequence, are diagnostic for the presence of nucleic acid sequences from maize event MON810 in said sample.

The foregoing and other aspects of the invention will become more apparent from the following detailed description and accompanying drawings.

DETAILED DESCRIPTION OF THE PREFERRED EMBODIMENTS

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994. The nomenclature for DNA bases as set forth at 37 CFR §1.822 is used.

As used herein, the term "comprising" means "including but not limited to".

Event

As used herein a transgenic "event" refers to a recombinant plant produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that include the heterologous DNA. Even after repeated backcrossing to a recurrent parent, the inserted DNA and flanking DNA from the transformed parent is present in the progeny of the cross at the same chromosomal location. The term "event" also refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

Probes and Primers

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from corn event, MON810 (whether from a corn plant or from a sample that includes DNA from the event). Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs or sets can be used for amplification of a nucleic acid sequence, e.g., by the polymerase chain reaction (PCR™), also known as thermal amplification methods, or other conventional nucleic-acid amplification methods.

Probes and primers are generally between 10 and 15 nucleotides or more in length, preferably 20 nucleotides or more, more preferably 25 nucleotides, and most preferably 30 nucleotides or more. Such probes and primers hybridize specifically to a target sequence under high stringency hybridization conditions. Preferably, probes and primers according to the present invention have complete sequence complementarity with the target sequence, although probes differing from the target sequence and which retain the ability to hybridize to target sequences may be designed by conventional methods.

Methods for preparing and using probes and primers are described, for example, in *Molecular Cloning: A Laboratory Manual*, 2nd ed., vol. 1–3, ed. Sambrook et al., Cold Spring Harbor Laboratory Press, Cold Spring Harbor, N.Y., 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992); and Innis et al., *PCR Protocols: A Guide to Methods and Applications*, Academic Press: San Diego, 1990. PCR™-primer pairs can be derived from a known sequence, for example, by using computer programs intended for that purpose such as Primer (Version 0.5, © 1991, Whitehead Institute for Biomedical Research, Cambridge, Mass.).

Primers and probes based on the flanking DNA and insert sequences disclosed herein can be used to confirm (and, if necessary, to correct) the disclosed sequences by conventional methods, e.g., by re-cloning and sequencing such sequences.

Nucleic-Acid Hybridization; "Stringent Conditions"; "Specific"

The nucleic-acid probes and primers of the present invention hybridize under stringent conditions to a target DNA sequence. Any conventional nucleic acid hybridization or amplification method can be used to identify the presence of DNA from a transgenic event in a sample.

The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52–9.55. See also, Sambrook et al., 1989 at 9.47–9.52, 9.56–9.58 herein incorporated by reference in its entirety; Kanehisa, (Nucl. Acids Res. 12:203–213, 1984, herein incorporated by reference in its entirety); and Wetmur and Davidson, (J. Mol. Biol. 31:349–370, 1988, herein incorporated by reference in its entirety). Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. One stringent condition, for example, is to wash the hybridization filter at least twice with high-stringency wash buffer (0.2×SSC, 0.1% SDS, 65° C.). Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Ser. Nos. 4,965,188 and 5,176,995 are exemplary of the methods of hybridization analyses.

Regarding the amplification of a target nucleic-acid sequence (e.g., by thermal amplification or PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic acid amplification of a target nucleic acid sequence that is part of a nucleic acid template. For example, to determine whether the corn plant resulting from a sexual cross contains a transgenic event, genomic DNA from a corn plant may be subjected to nucleic acid amplification using a primer pair that includes a primer derived from flanking sequence in the genome of the plant adjacent to the insertion site of inserted heterologous DNA and a second primer derived from the inserted heterologous DNA to produce an amplicon that is diagnostic for the presence of the event. The amplicon is of a length and has a sequence that is diagnostic for the event. Alternatively, a primer pair can be derived from flanking sequence on both sides of the inserted DNA so as to produce an amplicon that includes the entire insert.

Nucleic acid amplification can be accomplished by any of the various nucleic acid amplification methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. Any well known method for nucleic acid amplification may be used in the practice of the present invention. The sequence of the heterologous DNA insert or flanking sequence from corn MON810 event can be verified (and corrected if necessary) by amplifying such sequences from the event using primers derived from the sequences provided herein followed by standard methods of DNA sequencing of the PCR amplicon or of the cloned DNA molecule.

The amplicon produced by these methods may be detected by a plurality of techniques. Agarose gel electrophoresis and staining with ethidium bromide is a common well known method of detecting DNA amplicons. Another method is Genetic Bit Analysis (Nikiforov, et al. Nucleic Acid Res. 22:4167–4175, 1994) where an DNA oligonucleotide is designed which overlaps both the adjacent flanking genomic DNA sequence and the inserted DNA sequence. The oligonucleotide is immobilized in wells of a microtiter plate. Following thermal amplification of the region of interest (using one primer in the inserted sequence and one in the adjacent flanking genomic sequence), a single-stranded thermal amplification product can be hybridized to the immobilized oligonucleotide and serve as a template for a single base extension reaction using a DNA polymerase and labelled ddNTPs (dideoxynucleotides triphosphates) specific for the expected next base. Readout may be fluorescent or ELISA-based. A signal indicates presence of the insert/flanking sequence due to successful amplification, hybridization, and single base extension.

An additional method is the Pyrosequencing technique as described by Winge (Innov. Pharma. Tech. 00:18–24, 2000). In this method an oligonucleotide is designed that overlaps the adjacent genomic DNA and insert DNA junction. The oligonucleotide is hybridized to single-stranded thermal amplification product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. dNTPs (deoxynucleotide triphosphates) are added individually and the incorporation results in a light signal which is measured. A light signal indicates the presence of the transgene/flanking sequence due to successful amplification, hybridization, and single or multi-base extension.

Fluorescence Polarization as described by Chen, et al., (Genome Res. 9:492–498, 1999) is a method that can be used to detect the amplicon of the present invention. Using this method an oligonucleotide is designed which overlaps the genomic flanking and inserted DNA junction. The oligonucleotide is hybridized to a single-stranded thermal amplification product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene/flanking sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the genomic flanking and insert DNA junction. The FRET probe and thermal amplification primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene sequence due to successful amplification and hybridization.

Molecular Beacons have been described for use in sequence detection as in Tyangi, et al. (Nature Biotech.14:303–308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and thermal amplification primers (one primer in the insert DNA sequence and one in the flanking genomic sequence) are cycled in the presence of a thermostable polymerase and dNTPs. Following successful thermal amplification, hybridization of the FRET probe to the target sequence results in the removal of the probe secondary structure and spatial separation of the fluorescent and quenching moieties. A fluorescent signal results. A fluorescent signal indicates the presence of the flanking/transgene sequence due to successful amplification and hybridization.

Detection Kit

As used herein, "detection kit" refers to a kit used to detect the presence or absence of DNA from a MON810 event in a sample comprising nucleic-acid probes and primers of the present invention, which hybridize under stringent conditions to a target DNA sequence, and other materials necessary to enable nucleic acid hybridization or amplification methods. Alternatively, a detection kit may comprise materials necessary to enable one skilled in the art to perform methods similar to those described in PCT International Application WO 97/22719, incorporated herein by reference, to detect the presence or absence of DNA from a MON810 event in a sample.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

YieldGard® corn event MON810 has been a highly successful commercial product for more than five years. YieldGard® corn event MON810 was generated by particle acceleration technology using plasmid pMON15772. pMON15772 contained a single DNA sequence comprising tandem expression cassettes, in which is, at its arbitrarily assigned 5' end a first expression cassette encoding a neomycin phosphotransferase enzyme for use as a selectable marker, and a linked at the 3' end to a second expression cassette encoding an synthetically derived allele encoding a Cry1Ab insecticidal protein. The first expression cassette is comprised of a CaMVe35S promoter operably linked to a sequence encoding a neomycin phosphotransferase enzyme useful as a selectable marker, further operably linked to a nopaline synthase 3' end transcription termination and polyadenylation sequence. The second expression cassette is comprised of a CaMVe35S promoter sequence operably linked to a 5' untranslated sequence and a maize HSP70 intron sequence, operably linked to a synthetically derived nucleotide sequence comprising an allele of a cry1Ab lepidopteran specific insecticidal protein, further operably linked to a nopaline synthase 3' transcription termination and polyadenylation sequence. Molecular characterization of event MON810 DNA, and in particular analysis of the inserted DNA sequences as well as the immediately adjacent 200–500 or so nucleotides flanking either end of the inserted sequence, as indicated herein, reveals that the 5' distal 316 base pairs of the original 5' sequence of the 35S promoter driving expression of the NPTII coding sequence is not present within the inserted DNA sequence, but instead only the 3' most 299 base pairs of the e35S promoter are present at the arbitrarily assigned 5' end of the DNA sequence inserted into and incorporated as the MON810 event. In addition, the 3' end of the second expression cassette, i.e., the arbitrarily assigned 3' end of the intended insertion sequence, does not contain any sequence related to the NOS3' termination sequence, and additionally does not contain a significant portion of the 3' end of the coding sequence for the insecticidal protein encoded by the cry1Ab allele. Instead, only the 5' most 2448 base pairs of the cry1Ab allele encoding the amino terminal portion of the insecticidal protein are present within the inserted sequence of the MON810 event. Six nucleotides immediately adjacent to the 3' end of the intended inserted sequence which are derived from the plant genomic DNA sequence at the 3' junction sequence form two amino acid codons which are in frame with the remaining amino terminal coding sequence of the insecticidal protein upstream of these six nucleotides. The next three nucleotides form a translation termination codon. Therefore, the insecticidal protein which is expressed from this inserted insecticidal protein coding sequence is less than full length and encodes an insecticidal protein which contains at its carboxy terminus, two additional amino acids derived from plant coding sequences in place of the intended about 100 to 110 amino acids within the carboxy terminus of the synthetic insecticidal protein coding sequence present in the second cassette within pMON15772. There is no evidence, based on thermal amplification methods or hybridization methods, that any other portion of plasmid pMON15772 DNA has been integrated elsewhere into the corn genome. In order to develop event-specific identification methods using thermal amplification techniques, the sequence of corn DNA flanking the 5' and 3' ends of the insert in event MON810 was determined.

The isolation of genomic DNA from corn event MON810 and from the isogenic non-transformed corn line was performed following a modified procedure of Rogers and Bendich (1985) incorporated herein by reference. Corn grain was ground to a fine powder with a blender. About 6 grams of powder was transferred to a 50 milliliter centrifuge tube. Sixteen milliliters of CTAB extraction buffer [1.5% (w/v) CTAB, 75 mM Tris-HCl, pH 8.0, 100 mM EDTA, 1.05 M NaCl and 0.75% (w/v) PVP (MW 40,000)] was added to the powder, and the mixture was incubated at 65° C. for 30 minutes and allowed to cool at room temperature for 5 minutes. An equal volume (about 16 milliliters) of chloroform:isoamyl alcohol (24:1, v/v) was added to the sample and the suspension was mixed by inversion and centrifuged for 10 minutes at 10,000×g. The upper, aqueous phase was transferred to a clean 50 milliliter centrifuge tube. Approximately 1.6 milliliters (1/10 volume) of 10% (w/v) CTAB with 0.7 M NaCl were added to the supernatant and mixed. An equal volume (again, about 16 milliliters) of isopropanol was added to the tube and mixed by inversion for 5 minutes. The tube was centrifuged for 5 minutes at room temperature at 10,000×g. The supernatant was transferred to a clean 50 milliliter tube and mixed with an equal volume of CTAB precipitation buffer (1% CTAB (w/v), 50 mM Tris-HCl, pH 8.0 and 10 mM EDTA). The tube was maintained at room temperature for 1 hour and then centrifuged at 10,000×g for 10 minutes, also at room temperature. The supernatant was discarded and the pellet was resuspended in 2 milliliters of high salt TE (10 mM Tris-HCl, pH 8.0, 10 mM EDTA and 1 M NaCl). The sample was incubated at 37° C. for about 2 hours with gentle swirling and then centrifuged at 23,000×g for 2 minutes at room temperature. The supernatant was transferred to a clean 50 milliliter tube, and 150 milliliters of 3 M sodium acetate and 4 milliliters of 100% ethanol was added to the solution and mixed by inversion. The DNA was removed with a glass hook and placed in a 1.5 milliliter microcentrifuge tube along with 1 milliliter of 75% ethanol. The DNA was pelleted by centrifugation at 14,000×g for 2 minutes. The DNA pellet was vacuum dried for 5 minutes and resuspended in 200 milliliters of TE buffer [10 mM Tris-HCl, pH 8.0, and 1 mM EDTA]. DNA preparations were stored at 4° C. Extracted DNA was quantitated using Hoefer's DyNA Quant 200 Fluorometer with Boehringer Mannheim's DNA Molecular Weight Marker IX as the standard.

DNA extracted from the MON810 event was compared to DNA from an untransformed isogenic corn plant line as well as to restriction enzyme digested pMON15772. Southern blot analysis indicated that the inserted sequence was somewhat smaller than the sequence within pMON15772 comprising the two tandem expression cassettes. Analysis of each expression cassette by southern blot also indicated that each cassette was shorter than the parent cassette from which the insertion sequence was derived, however, digestion of the tandem expression cassette sequence and Southern blot probe analysis indicated that the interior of the tandem expression cassette was intact. Therefore, primers were designed based on the southern blot analyses, which allowed primer extension walking out of the insert sequence from either end of the inserted DNA sequence into the flanking corn plant genome sequence. In this way, the arbitrarily defined 5' and 3' ends of the inserted DNA in MON810 were precisely identified along with the junction of each end of the insert with the genomic DNA into which the heterologous DNA was inserted.

As disclosed herein and set forth in SEQ ID NO:3, the first 244 nucleotides of SEQ ID NO:3 represent genomic corn DNA 5' of and adjacent to the 5' end of the inserted DNA, and nucleotides 245 through 566 represent a portion of the e35S promoter which is driving expression of the DNA sequence encoding the selectable marker, NPTII. The 5' junction sequence therefore, can be represented by nucleotides 1 through 20 as set forth in SEQ ID NO:1, and more particularly by nucleotides 244 through 245 as set forth in SEQ ID NO:3.

Also, as disclosed herein and set forth in SEQ ID NO:4, nucleotides 274–879 represent corn genomic DNA sequence immediately adjacent to and flanking the 3' end of the inserted DNA sequence in event MON810. Nucleotides 1 through 273 as set forth in SEQ ID NO:4 represent the 3' terminal sequence of the inserted heterologous DNA in MON810. Nucleotides 274–279 represent the codons encoding the additional two amino acids added to the less than full length insecticidal protein expressed from the second expression cassette which originated from pMON15772. Nucleotides 280–282 represent the termination codon which terminates translation of the insecticidal protein produced in corn event MON810. Therefore, the 3' junction sequence of the inserted heterologous DNA in event MON810 can be represented by the nucleotides 1–20 as set forth in SEQ ID NO:2, and more particularly by nucleotides 273–274 as set forth in SEQ ID NO:4.

In order to determine the nucleotide sequence in the non-transformed and isogenic corn DNA, the DNA sequence across the insertion site was obtained. A primer pair for use in amplifying across this sequence was designed based on the 5' flanking sequence and the 3'flanking sequence within the MON810 corn genome. SEQ ID NO:7 corresponds to the first 18 nucleotides of the 5' end of SEQ ID NO:3, which is within the corn genome beyond the arbitrarily assigned 5' end of the inserted heterologous DNA sequence. SEQ ID NO:10 corresponds to the last 28 nucleotides of SEQ ID NO:4, and is shown as the reverse complement of the sequence as set forth in SEQ ID NO:4. Based on the 5' end genomic sequence information from MON810, and the 3' end genomic sequence information from MON810, primers comprising SEQ ID NO:7 and SEQ ID NO:10 should amplify a sequence comprising 849 nucleotides from within the non-transformed isogenic corn line, corresponding to the first 244 nucleotides of SEQ ID NO:3 and the last 605 nucleotides of SEQ ID NO:4.

Thermal amplification analysis of the arbitrarily assigned 5' end of the insert in event MON810 was performed using a primer pair consisting of a first primer, SEQ ID NO:7, corresponding to the first 18 nucleotides of the 5' end of SEQ ID NO:3, and a second primer, the reverse complement of SEQ ID NO:8, corresponding to the last 20 nucleotides of SEQ ID NO:3 located within the 5' end of the inserted heterologous DNA sequence. The amplicon formed using these primers and a template consisting of event MON810 DNA consists of a nucleotide sequence of 566 base pairs as set forth in SEQ ID NO:3. Alternatively, thermal amplification analysis of the 5' end of the insert in event MON810 can be performed using any primer pair sufficient to produce an amplicon which is diagnostic for the MON810 event, comprising an isolated nucleic acid comprising from about 10 to about 15 or more contiguous nucleotides derived from the 5' genomic flanking sequence paired with any second primer comprising from about 10 to about 15 or more contiguous nucleotides located within the insert.

Thermal amplification analysis of the arbitrarily assigned 3' end of the insert in event MON810 was performed using a primer pair consisting of a first primer, SEQ ID NO:9, corresponding to the first 28 nucleotides of the 5' end of the sequence as set forth in SEQ ID NO:4, and a second primer, the reverse complement of SEQ ID NO:10, corresponding to the last 28 nucleotides of the 3' end of the sequence as set forth in SEQ ID NO:4. The amplicon formed using these primers and a template consisting of event MON810 DNA consists of a nucleotide sequence of 879 base pairs as set forth in SEQ ID NO:4. Alternatively, thermal amplification analysis of the 3' end of the insert in event MON810 can be performed using any primer pair sufficient to produce an amplicon which is diagnostic for the MON810 event, comprising an isolated nucleic acid comprising from about 10 to about 15 or more contiguous nucleotides derived from the 3' genomic flanking sequence paired with any second primer comprising from about 10 to about 15 or more contiguous nucleotides located within the insert.

Thermal amplification analyses were performed using about 100 ng of MON810 genomic DNA template in a 50 $\mu$l reaction volume. Each reaction contained 10 mM Tris-HCl, 50 mM KCl, 1.5 mM $MgCl_2$, 200 $\mu$M of each dNTP, 0.2 mM each primer, and 5 units of Taq DNA polymerase. The reactions were performed under the following cycling conditions: 1 cycle at 94° C. for 5 minutes; 38 cycles at 94° C. for 30 seconds, 58° C. for 30 seconds and 72° C. for 1.5 minutes; 1 cycle at 72° C. for 5 minutes. Ten microliters of each reaction were separated on a 1.0% agarose gel in 1×

TAE (40 mM Tris-acetate, 20 mM glacial acetic acid, 10 mM EDTA, pH 8.4) at 100 V for about 1 hour. The thermal amplification products, or resulting amplicons, were visualized by ethidium bromide staining under UV illumination and compared to a 100 base pair ladder.

Thermal amplification products (amplicons) of the expected sizes (566 bp and 879 bp), representing the 5' and 3' flanking sequences, respectively, were excised from the gel and purified using the Geneclean II Gel Extraction System (BIO 101), following the procedure supplied by the manufacturer. The purified amplicons were sequenced using the primers described above.

Amplicon analyses were performed on genomic DNA extracted from YieldGard® corn event MON810 and non-transgenic corn line B73 to verify the DNA sequences flanking the 5' and 3' ends of the insert in corn event MON810. The control reactions containing no DNA template as well as the reactions containing B73 non-transgenic corn DNA did not generate a amplicon with either primer set described above, as expected. Thermal amplifications with event MON810 DNA generated products of the expected sizes of 566 bp representing the 5' flanking sequence and 879 bp representing the 3' flanking sequence. These results demonstrate that the amplicon products of predicted sizes are generated from both ends of the insert in YieldGard® corn event MON810.

The sequences of the amplicon products, representing the genomic DNA flanking the 5' and 3' ends of the insert, are presented in SEQ ID NO:3 and SEQ ID NO:4, respectively. Sequence data show that the 5' amplicon consists of 244 bp of corn genomic flanking DNA followed by 299 bp of the enhanced CaMV 35S promoter and 23 bp of linker DNA at the junction of the promoter and HSP70 intron. The 3' amplicon consists of 273 bp of the insecticide coding sequence followed by 606 bp of corn genomic flanking DNA.

Having described and illustrated the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference herein.

References

Rogers, S. O. and Bendich, A. J. 1985. Extraction of DNA from milligram amounts of fresh, herbarium and mummified plant tissues. Plant Mol. Biol. 5:69–76.

---

What is claimed is:

1. An isolated polynucleotide selected from the group consisting of SEQ ID NO:2, SEQ ID NO:1, and complements thereof.

2. A pair of polynucleotide primers for use in producing in a thermal amplification reaction an amplicon diagnostic for the presence of corn event MON810 DNA in a sample comprising
   (a) a first primer consisting of 15 contiguous nucleotides from position 1–244 as set forth in SEQ ID NO:3; and
   (b) a second primer consisting of 15 contiguous nucleotides complementary to position 245–566 as set forth in SEQ ID NO:3,
   wherein said amplicon consists at least of a contiguous 30 nuclcotide sequence as set forth in SEQ ID NO:3 from position 1 through position 566 and comprises SEQ ID NO:1.

3. A pair of polynucleotide primers for use in producing in a thermal amplification reaction an amplicon diagnostic for the presence of corn event MON810 DNA in a sample comprising
   (a) a first primer consisting of 15 contiguous nucleotides from position 1–273 as set forth in SEQ ID NO:4; and
   (b) a second primer consisting of 15 contiguous nucleotides complementary to position 274–879 as set forth in SEQ ID NO:4,
   wherein said amplicon consists at least of a 30 contiguous nucleotide sequence as set forth in SEQ ID NO:4 from position 1 through position 879 and comprises SEQ ID NO:2.

4. A method of detecting a DNA sequence in a sample, the method comprising:
   (a) contacting said sample with a pair of primers that, when used in a nucleic-acid amplification reaction with DNA from corn event MON810, produces an amplicon that is diagnostic for corn event MON810;
   (b) performing a nucleic acid amplification reaction, thereby producing the amplicon; and
   (c) detecting the amplicon;
   wherein said pair of primers is selected from the group consisting of (1) a first primer consisting of 15 contiguous nucleotides from position 1–244 as set forth in SEQ ID NO:3 and a second primer consisting of 15 contiguous nucleotides complementary to position 245–566 as set forth in SEQ ID NO:3, and (2) a first primer consisting of 15 contiguous nucleotides from position 1–273 as set forth in SEQ ID NO:4 and a second primer consisting of 15 contiguous nucleotides complementary to position 274–879 as set forth in SEQ ID NO:4.

5. A kit for detecting the presence of a nucleotide sequence in a biological sample, said kit comprising (1) a nucleotide probe which is or is fully complementary to a sequence selected from the group consisting of SEQ ID NO:1 or SEQ ID NO:2, and (2) a pair of primers for use in a nucleic-acid amplification reaction, said pair of primers being selected from the group consisting of (a) a first primer consisting of 15 contiguous nucleotides from position 1–244 as set forth in SEQ ID NO:3 and a second primer consisting of 15 contiguous nucleotides complementary to position 245–566 as set forth in SEQ ID NO:3, and (2) a first primer consisting of 15 contiguous nucleotides from position 1–273 as set forth in SEQ ID NO:4 and a second primer consisting of 15 contiguous nucleotides complementary to position 274–879 as set forth in SEQ ID NO:4.

6. The method according to claim 4 wherein said pair of primers in (1) are SEQ ID NO:7 and the reverse complement of SEQ ID NO:8, and wherein said pair of primers in (2) are SEQ ID NO:9 and the reverse complement of SEQ ID NO:10.

7. A method for detecting a nucleotide sequence in a biological sample, said method comprising:
   (a) contacting said sample with a probe that hybridizes under stringent hybridization conditions with said nucleotide sequence;
   (b) subjecting the sample and probe to stringent hybridization conditions; and
   (c) detecting hybridization of the probe to the nucleotide sequence;
   wherein step (c) is indicative of the presence of said nucleotide sequence; and
   wherein said probe consists of a sequence selected from the group consisting of SEQ ID NO:1, SEQ ID NO:2, and complements thereof.

8. A method for detecting in a biological sample the presence of a target site in a nucleotide sequence, said method comprising the steps of
   (a) contacting said sample with a probe that hybridizes under stringent hybridization conditions with said target site;
   (b) subjecting the sample and probe to stringent hybridization conditions; and
   (c) detecting hybridization of the probe to the target site;
   wherein step (c) is indicative of the presence of said target site; and
   wherein said target site comprises a sequence selected from the group consisting of SEQ ID NO:1, SEQ ID NO:2, and the complements thereof; and
   wherein said probe is a polynucleotide which is or is complementary to a nuclcotide selected from the group consisting of SEQ ID NO:1 and SEQ ID NO:2.

9. A method for detecting the presence of a junction sequence in corn event MON810, said sequence being the junction between heterologous DNA inserted into a corn genome and corn genome DNA flanking the insertion site, detection of said sequence being diagnostic for the event, said method comprising amplifying in a thermal reaction DNA present in a biological sample using:

(a) a first primer pair, each member of the first primer pair consisting of at least 10–15 contiguous nucleotides in length, the first member of the first primer pair being selected from the group of nucleotides as set forth in SEQ ID NO:3 from position 1 through 244, and the second member of the first primer pair being selected from the heterologous DNA inserted into the corn genome; and (b) a second primer pair, each member of the second primer pair consisting of at least 10–15 contiguous nucleotides in length, the first member of the second primer pair being selected from the heterologous DNA inserted into the corn genome and the second member of the second primer pair being selected from the group of nucleotides complementary to those as set forth in SEQ ID NO:4 from position 274 through 879;

wherein use of the first or the second primer pair in said thermal amplification reaction along with a biological sample comprising MON810 DNA produces an amplicon that is diagnostic for the MON810 event in said sample, and wherein said amplicon produced from the use of said first primer pair comprises SEQ ID NO:1, and said amplicon produced from the use of said second primer pair comprises SEQ ID NO:2, wherein detecting said amplicon comprising SEQ ID NO:1 and said amplicon comprising SEQ ID NO:2 is indicative of the presence of said junction sequence.

10. The method of claim 9 wherein said first member of said first primer pair consists of SEQ ID NO:7 and said second member of said first primer pair consists of SEQ ID NO:8, and wherein said first member of said second primer pair consists of SEQ ID NO:9 and said second member of said second primer pair consists of SEQ ID NO:10.

11. A method for detecting the presence of a junction sequence in corn event MON810, said sequence being the junction between heterologous DNA inserted into a corn genome and corn genome DNA flanking the insertion site, said sequence being diagnostic for the event, said method comprising amplifying in a thermal reaction DNA present in a biological sample using:

(a) a first primer pair, each member of the first primer pair consisting of at least 10 to 15 contiguous nucleotides in length, the first member of the first primer pair being selected from the group of nucleotides as set forth in SEQ ID NO:3 from position 1 through 244, and the second member of the first primer pair being selected from the heterologous DNA inserted into the corn genome, said second member of the first primer pair being selected from the complement of the nucleotide sequence as set forth in SEQ ID NO:3 from position 245 through 566; and (b) a second primer pair, each member of the second primer pair consisting of at least 10–15 contiguous nucleotides in length, the first member of the second primer pair being selected from the heterologous DNA inserted into the corn genome, said first member of the second primer pair being selected from the nucleotide sequence as set forth in SEQ ID NO:4 from position 1 through 273, and the second member of the second primer pair being selected from the group of nucleotides complementary to those as set forth in SEQ ID NO:4 from position 274 through 879;

wherein use of the first or the second primer pair in said thermal amplification reaction along with a biological sample comprising MON810 DNA produces an amplicon that is diagnostic for the MON810 event in said sample, and wherein said amplicon produced from the use of said first primer pair comprises SEQ ID NO:1, and said amplicon produced from the use of said second primer pair comprises SEQ ID NO:2, wherein detecting said amplicon comprising SEQ ID NO:1 and said amplicon comprising SEQ ID NO:2 is indicative of the presence of said junction sequence.

12. The method of claim 11 wherein said first member of said first primer pair consists of SEQ ID NO:7 and said second member of said first primer pair consists of SEQ ID NO:8, and said first member of said second primer pair consists of SEQ ID NO:9 and said second member of said second primer pair consists of SEQ ID NO:10.

13. A kit comprising a pair of polynucleotide primers for use in detecting the presence of a target sequence in a sample, wherein said pair of polynucleotide primers hybridize specifically to SEQ ID NO:3 or to SEQ ID NO:4 or the full complements thereof and are extended toward each other to form an amplicon which contains the target sequence, said target sequence being selected from the group consisting of SEQ ID NO:1 and SEQ ID NO:2.

* * * * *